United States Patent
Liniger

(10) Patent No.: US 12,195,698 B2
(45) Date of Patent: Jan. 14, 2025

(54) FRAGRANCE COMPOUND PROVIDING LILY OF THE VALLEY FRAGRANCE CHARACTERISTICS, AND FRAGRANCED COMPOSITIONS COMPRISING THE SAME

(71) Applicant: GIVAUDAN SA, Vernier (CH)

(72) Inventor: Marc Liniger, Embrach (CH)

(73) Assignee: Givaudan SA, Vernier (CH)

( * ) Notice: Subject to any disclaimer, the term of this patent is extended or adjusted under 35 U.S.C. 154(b) by 643 days.

(21) Appl. No.: 17/437,969

(22) PCT Filed: Mar. 27, 2020

(86) PCT No.: PCT/EP2020/058653
§ 371 (c)(1),
(2) Date: Sep. 10, 2021

(87) PCT Pub. No.: WO2020/201052
PCT Pub. Date: Oct. 8, 2020

(65) Prior Publication Data
US 2022/0186140 A1 Jun. 16, 2022

(30) Foreign Application Priority Data
Apr. 1, 2019 (GB) ...................... 1904533

(51) Int. Cl.
*C11B 9/00* (2006.01)
*C07C 47/267* (2006.01)

(52) U.S. Cl.
CPC .......... *C11B 9/0034* (2013.01); *C07C 47/267* (2013.01); *C07C 2601/16* (2017.05)

(58) Field of Classification Search
CPC .. C11B 9/0034; C07C 47/367; C07C 2601/16
USPC .................................. 512/22, 8, 1
See application file for complete search history.

(56) References Cited

U.S. PATENT DOCUMENTS

| | | |
|---|---|---|
| 4,007,137 A | 2/1977 | Sanders |
| 2018/0201873 A1* | 7/2018 | Coulomb .................. A61K 8/34 |
| 2019/0249111 A1* | 8/2019 | Walther ................. C11B 9/0061 |
| 2019/0276769 A1* | 9/2019 | Saudan .................. C11B 9/0061 |
| 2021/0101860 A1* | 4/2021 | Coulomb .............. C11B 9/0034 |

FOREIGN PATENT DOCUMENTS

| | | | |
|---|---|---|---|
| EP | 1054053 A1 | 11/2000 | |
| WO | 202002212 A1 | 1/2010 | |
| WO | WO-2017009175 A1 * | 1/2017 | ............... A61K 8/34 |
| WO | 2018157200 A1 | 9/2018 | |
| WO | 2019015974 A1 | 1/2019 | |

OTHER PUBLICATIONS

International Search Report and Written Opinion of the International Searching Authority for corresponding application PCT/EP2020/058653 dated Jun. 3, 2020.

* cited by examiner

*Primary Examiner* — Jessica Whiteley
(74) *Attorney, Agent, or Firm* — Norris McLaughlin, PA

(57) ABSTRACT

A compound according to formula I in the form of any one of its stereoisomers or a mixture thereof

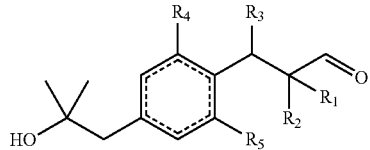

formula (I)

wherein

------- is indicating a carbon-carbon single or double bond, with the provision that the compound has one carbon-carbon double bond or two isolated or conjugated carbon-carbon double bonds, and $R_1$ to $R_5$ are independently from each other selected from H or Me, with the proviso that the compound is not 3-(4-(2-hydroxy-2-methylpropyl)cyclohex-1-en-1-yl)propanal, and its use as fragrance.

17 Claims, No Drawings

FRAGRANCE COMPOUND PROVIDING LILY OF THE VALLEY FRAGRANCE CHARACTERISTICS, AND FRAGRANCED COMPOSITIONS COMPRISING THE SAME

This is an application filed under 35 USC 371 based on PCT/EP2020/058653 (WO 2020/201052), filed 27. Mar. 2020, which in turn is based on GB 1904533.5 filed 01. Apr. 2019. The present application claims the full priority benefit of these prior applications and herein incorporates by reference the full disclosures of these prior applications.

The present invention is directed to novel organic compounds, a method of preparing said compounds and their use as fragrance ingredients, in particular their use as a fragrance ingredient to impart a muguet odour characteristic to a perfume composition. The invention also relates to perfume compositions and to articles, such as fine fragrances or consumer product compositions perfumed by the compounds, or the perfume compositions containing said compounds.

BACKGROUND OF THE INVENTION

Compounds having muguet (or lily of the valley) odour characteristics are very sought after as perfume ingredients. These compounds are important ingredients in floral bases and can act as harmonizers across many types of fragrance creations. Compounds of this type are used widely in personal care and consumer care products, as well as in fine perfumery, to generate pleasant odours or to mask unpleasant odours.

An excellent perfume ingredient widely valued for its muguet odour note is 4-(4-hydroxy-4-methylpentyl) 3-cyclohexene carboxaldehyde, otherwise known as cyclohexal (Lyral™). This compound has found wide use in fine perfumery as well as in personal and household care products. However according to findings of the European Scientific Committee for Consumer Safety (SCCS) it has allergenic concerns and at the present time its use in cosmetics is subject to regulatory action in the EU.

So there remains a need to develop novel fragrance ingredients to replace Lyral™.

WO 2017/009175 reports potential replacer compounds for Lyral™. Those aromatic compounds are reported to be powerful, substantive, and to provide the "wet" aspect of Lyral™. Two example compounds 3-(4-(2-hydroxy-2-methylpropyl)-2-methylphenyl)propanal and 3-(4-(2-hydroxy-2-methylpropyl)phenyl)propanal are disclosed, amongst others.

There remains the need to provide novel fragrance ingredients suitable for different uses in perfumery.

The present invention provides novel fragrance ingredients with a relatively low odour threshold, imparting lily of the valley notes, so far not reported in the prior art.

DESCRIPTION OF THE INVENTION

Surprisingly it was now found that compounds of the invention have a powerful and long-lasting lily-of-the-valley odour with clean and very diffusive notes especially appreciated in Lyral.

In a first aspect of the invention, there is provided a compound according to formula (I) in the form of any one of its stereoisomers or a mixture thereof

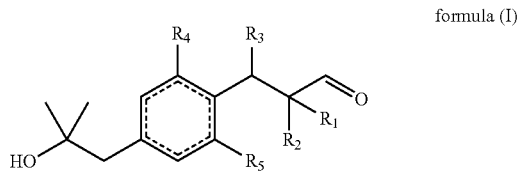

formula (I)

wherein

------ is indicating a carbon-carbon single or double bond, with the provision that the compound has one carbon-carbon double bond or two isolated or conjugated carbon-carbon double bonds, and $R_1$ to $R_5$ are independently from each other selected from H or Me, with the proviso that the compound is not 3-(4-(2-hydroxy-2-methylpropyl)cyclohex-1-en-1-yl)propanal.

It couldn't be expected that the partially saturated compound of the invention is showing fragrance properties comparable to those of the aromatic derivatives known from prior art. While the aromatic ring is flat, a partially saturated ring system is bent, changing the overall molecular structure significantly. It is expected, that the fragrance properties as odour and odour strength, should be modified as well. Surprisingly, the compounds of the invention have a powerful and long-lasting lily-of-the-valley odour with clean and very diffusive notes especially appreciated in Lyral. The odour threshold value remains comparable. In contrast to that, the fully saturated analogues have been found to be considerably weaker odourants (having a higher odour threshold value) with some floral muguet aspects.

Beside similar odour and odour strength, the compound of the present invention has a more transparent odour when compared to aromatic analogues. This difference is causing a more natural effect, and rendering the compound more versatile. In contrast to opaque compounds in general, the compound of the invention is suitable for use in consumer products but also for use in fine fragrance. Transparent compounds typically blend nicely into a fragrance accord, and they support the overall trail and volume of a perfume. So the compound of the invention provides distinguishable characteristics over molecules known from prior art.

As used herein, "GC threshold value" (GCTH) means the lowest concentration of a vapour in the air which can be detected by smell. Generally speaking, it can be said that a compound with a low threshold value is more powerful than a compound with a high threshold value and thus allows the use of very low concentration in a perfume composition to achieve an olfactory effect.

The compound of formula (I) (and also of the following formulae) may comprise one or more chiral centers and as such may exist as a mixture of stereoisomers (enantiomers and diastereoisomers), or may be resolved as pure stereoisomers. Resolving stereoisomers adds to the complexity of manufacture and purification of the compound, and so it is preferred to use the compound as mixture of its stereoisomers simply for economic reasons. However, if it is desired to prepare individual stereoisomers, this may be achieved according to methods known in the art, e.g. stereoselective synthesis, preparative HPLC and GC.

In a further aspect of the invention, there is provided a compound according to formula (II) in the form of any one of its stereoisomers or a mixture thereof

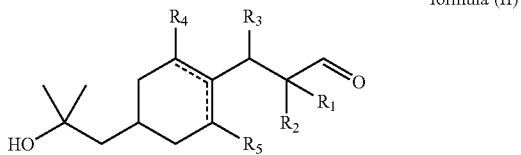

formula (II)

wherein

------ is indicating a carbon-carbon single or double bond, with the provision that the compound has one carbon-carbon double bond, and $R_1$ to $R_5$ are independently from each other selected from H or Me, with the proviso that the compound is not 3-(4-(2-hydroxy-2-methylpropyl)cyclohex-1-en-1-yl)propanal.

In a further aspect of the invention, there is provided a compound according to formula (III) in the form of any one of its stereoisomers or a mixture thereof

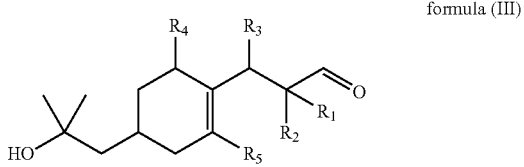

formula (III)

wherein $R_1$ to $R_5$ are independently from each other selected from H or Me, with the proviso that the compound is not 3-(4-(2-hydroxy-2-methylpropyl)cyclohex-1-en-1-yl) propanal.

In a further aspect of the invention, there is provided a compound according to formula (III) wherein $R_1$ is H, and $R_2$ to $R_5$ are independently from each other selected from H or Me, with the proviso that the compound is not 3-(4-(2-hydroxy-2-methylpropyl)cyclohex-1-en-1-yl)propanal.

In a further aspect of the invention, there is provided a compound according to formula (III) wherein $R_1$ and $R_2$ are H, and $R_3$ to $R_5$ are independently from each other selected from H or Me, with the proviso that the compound is not 3-(4-(2-hydroxy-2-methylpropyl)cyclohex-1-en-1-yl)propanal.

In a further aspect of the invention, there is provided a compound according to formula (III) wherein $R_1$ and $R_2$ are H, and $R_3$ to $R_5$ are independently from each other selected from H or Me, wherein one or two of said $R_3$ to $R_5$ may represent a hydrogen atom, and the other or others a hydrogen atom or a methyl group, with the proviso that the compound is not 3-(4-(2-hydroxy-2-methylpropyl)cyclohex-1-en-1-yl)propanal.

One specific, non-limiting example of the present invention is 3-(4-(2-hydroxy-2-methylpropyl)-2-methylcyclohex-1-en-1-yl)propanal, which shows a floral muguet odour, with a soft creamy powdery feel and a slight fresh aldehydic facet, and a GCTH value of 0.0033 ng.

Another specific, non-limiting example of the present invention is rel-3-((4R,6S)-4-(2-hydroxy-2-methylpropyl)-6-methylcyclohex-1-en-1-yl)propanal, which shows a soft, floral, muguet, white floral, soft, fresh, aldehydic, green, citrus odour, and a GCTH value of 0.003 ng.

Another specific, non-limiting example of the present invention is 3-(4-(2-hydroxy-2-methylpropyl)cyclohex-1-en-1-yl)-2-methylpropanal, with a floral, muguet, cyclohexal, white floral, transparent, clean odour, and a GCTH value of 0.018 ng.

For comparison, we determined the GCTH values of the aromatic analogues 3-(4-(2-hydroxy-2-methylpropyl)-2-methylphenyl)propanal and 3-(4-(2-hydroxy-2-methylpropyl)phenyl)propanal described in WO 2017/009175 to be in the same range, namely at 0.01 ng and 0.05 ng. In contrast, the fully saturated comparative compound 3-(4-(2-hydroxy-2-methylpropyl)cyclohexyl)propanal has a considerably higher GCTH value of 0.53 ng.

In a further aspect of the invention, there is provided a use as fragrance of a compound according to formula (I) or according to formula (II) in the form of any one of its stereoisomers or a mixture thereof.

In a further aspect of the invention, there is provided a use as fragrance of a compound according to formula (III) in the form of any one of its stereoisomers or a mixture thereof, wherein $R_1$ to $R_5$ are independently from each other selected from H or Me; or wherein $R_1$ is H, and $R_2$ to $R_5$ are independently from each other selected from H or Me; or wherein $R_1$ and $R_2$ are H, and $R_3$ to $R_5$ are independently from each other selected from H or Me; or wherein one or two of said $R_3$ to $R_5$ may represent a hydrogen atom, and the other or others a hydrogen atom or a methyl group.

In yet another aspect of the present invention, there is provided a perfume composition comprising a compound according to formula (I) or a compound according to formula (II) in the form of any one of its stereoisomers or a mixture thereof.

In a further aspect of the invention, there is provided a perfume composition comprising a compound according to formula (III) in the form of any one of its stereoisomers or a mixture thereof, wherein $R_1$ to $R_5$ are independently from each other selected from H or Me; or wherein $R_1$ is H, and $R_2$ to $R_5$ are independently from each other selected from H or Me; or wherein $R_1$ and $R_2$ are H, and $R_3$ to $R_5$ are independently from each other selected from H or Me; or wherein one or two of said $R_3$ to $R_5$ may represent a hydrogen atom, and the other or others a hydrogen atom or a methyl group.

The compounds of the invention may be used alone, or in combination with known odorant molecules selected from the extensive range of natural products, and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in perfume compositions, for example, carrier materials, and other auxiliary agents commonly used in the art.

As used herein, "carrier material" means a material which is practically neutral from a odorant point of view, i.e. a material that does not significantly alter the organoleptic properties of odorants.

The term "auxiliary agent" refers to ingredients that might be employed in a perfume composition for reasons not specifically related to the olfactive performance of said composition. For example, an auxiliary agent may be an ingredient that acts as an aid to processing a fragrance ingredient or ingredients, or a composition containing said ingredient(s), or it may improve handling or storage of a fragrance ingredient or composition containing same. It might also be an ingredient that provides additional benefits such as imparting color or texture. It might also be an ingredient that imparts light resistance or chemical stability to one or more ingredients contained in a perfume composition. A detailed description of the nature and type of adjuvants commonly used in perfume compositions containing same cannot be exhaustive, but it has to be mentioned that said ingredients are well known to a person skilled in the art.

As used herein, "perfume composition" means any composition comprising the compound of formula (I) and a base material, e.g. a diluent conventionally used in conjunction with odorants, such as diethyl phthalate (DEP), dipropylene glycol (DPG), isopropyl myristate (IPM), pentane-1,2-diol, triethyl citrate (TEC) and alcohol (e.g. ethanol). Optionally, the composition may comprise an anti-oxidant adjuvant. Said anti-oxidant may be selected from Tinogard® TT (BASF), Tinogard® Q (BASF), Tocopherol (including its isomers, CAS 59-02-9; 364-49-8; 18920-62-2; 121854-78-2), 2,6-bis(1,1-dimethylethyl)-4-methylphenol (BHT, CAS 128-37-0) and related phenols, hydroquinones (CAS 121-31-9).

The following list comprises examples of known odorant molecules, which may be combined with the compounds of formula (I):
essential oils and extracts, e.g. *castoreum, costus* root oil, oak moss absolute, *geranium* oil, tree moss absolute, basil oil, fruit oils, such as bergamot oil and mandarin oil, myrtle oil, palmarose oil, patchouli oil, petitgrain oil, jasmine oil, rose oil, sandalwood oil, wormwood oil, lavender oil and/or ylang-ylang oil;
alcohols, e.g. cinnamic alcohol ((E)-3-phenylprop-2-en-1-ol); cis-3-hexenol ((Z)-hex-3-en-1-ol); citronellol (3,7-dimethyloct-6-en-1-ol); dihydro myrcenol (2,6-dimethyloct-7-en-2-ol); Ebanol™ ((E)-3-methyl-5-(2,2,3-trimethylcyclopent-3-en-1-yl)pent-4-en-2-ol); eugenol (4-allyl-2-methoxyphenol); ethyl linalool ((E)-3,7-dimethylnona-1,6-dien-3-ol); farnesol ((2E,6Z)-3,7,11-trimethyldodeca-2,6,10-trien-1-ol); geraniol ((E)-3,7-dimethylocta-2,6-dien-1-ol); Super Muguet™ ((E)-6-ethyl-3-methyloct-6-en-1-ol); linalool (3,7-dimethylocta-1,6-dien-3-ol); menthol (2-isopropyl-5-methylcyclohexanol); Nerol (3,7-dimethyl-2,6-octadien-1-ol); phenyl ethyl alcohol (2-phenylethanol); Rhodinol™ (3,7-dimethyloct-6-en-1-ol); Sandalore™ (3-methyl-5-(2,2,3-trimethylcyclopent-3-en-1-yl)pentan-2-ol); terpineol (2-(4-methylcyclohex-3-en-1-yl)propan-2-ol); or Timberol™ (1-(2,2,6-trimethylcyclohexyl)hexan-3-ol); 2,4,7-trimethylocta-2,6-dien-1-ol, and/or [1-methyl-2(5-methylhex-4-en-2-yl)cyclopropyl]-methanol;
aldehydes and ketones, e.g. anisaldehyde (4-methoxybenzaldehyde); alpha amyl cinnamic aldehyde (2-benzylideneheptanal); Georgywood™ (1-(1,2,8,8-tetramethyl-1,2,3,4,5,6,7,8-octahydronaphthalen-2-yl)ethanone); Hydroxycitronellal (7-hydroxy-3,7-dimethyloctanal); Iso E Super® (1-(2,3,8,8-tetramethyl-1,2,3,4,5,6,7,8-octahydronaphthalen-2-yl)ethanone); Isoraldeine® ((E)-3-methyl-4-(2,6,6-trimethylcyclohex-2-en-1-yl)but-3-en-2-one); Hedione® (methyl 3-oxo-2-pentylcyclopentaneacetate); 3-(4-isobutyl-2-methylphenyl)propanal; maltol; methyl cedryl ketone; methylionone; verbenone; and/or vanillin;
ether and acetals, e.g. Ambrox® (3a,6,6,9a-tetramethyl-2,4,5,5a,7,8,9,9b-octahydro-1H-benzo[e][1]benzofuran); geranyl methyl ether ((2E)-1-methoxy-3,7-dimethylocta-2,6-diene); rose oxide (4-methyl-2-(2-methylprop-1-en-1-yl)tetrahydro-2H-pyran); and/or Spirambrene® (2',2',3,7,7-pentamethylspiro[bicyclo [4.1.0]heptane-2,5'-[1,3]dioxane]);
esters and lactones, e.g. benzyl acetate; cedryl acetate ((1S,6R,8aR)-1,4,4,6-tetramethyloctahydro-1H-5,8a-methanoazulen-6-yl acetate); γ-decalactone (6-pentyltetrahydro-2H-pyran-2-one); Helvetolide® (2-(1-(3,3-dimethylcyclohexyl)ethoxy)-2-methylpropyl propionate); γ-undecalactone (5-heptyloxolan-2-one); and/or vetiveryl acetate ((4,8-dimethyl-2-propan-2-ylidene-3,3a,4,5,6,8a-hexahydro-1H-azulen-6-yl) acetate);
macrocycles, e.g. Ambrettolide ((Z)-oxacycloheptadec-10-en-2-one); ethylene brassylate (1,4-dioxacycloheptadecane-5,17-dione); and/or Exaltolide® (16-oxacyclohexadecan-1-one); and
heterocycles, e.g. isobutylquinoline (2-isobutylquinoline).

In yet another aspect of the present invention, there is provided a perfumed article, such as a fine fragrance or a personal or household care product, perfumed with a compound of formula (I) or a compound according to formula (II) in the form of any one of its stereoisomers or a mixture thereof.

In a further aspect of the invention, there is provided a perfumed article, such as a fine fragrance or a personal or household care product, perfumed with a compound of formula (III) in the form of any one of its stereoisomers or a mixture thereof, wherein $R_1$ to $R_5$ are independently from each other selected from H or Me; or wherein $R_1$ is H, and $R_2$ to $R_5$ are independently from each other selected from H or Me; or wherein $R_1$ and $R_2$ are H, and $R_3$ to $R_5$ are independently from each other selected from H or Me; or wherein one or two of said $R_3$ to $R_5$ may represent a hydrogen atom, and the other or others a hydrogen atom or a methyl group.

The compound of the invention may be used in a broad range of perfumed articles, e.g. in any field of fine and functional perfumery, such as perfumes, air care products, household products, laundry products, body care products and cosmetics. The compound can be employed in widely varying amounts, depending upon the specific article and on the nature and quantity of other odorant ingredients. The proportion is typically from 0.0001 to 3 weight percent of the article. In one embodiment, the compound of the present invention may be employed in a fabric softener in an amount from 0.001 to 0.3 weight percent (e.g. 0.01 to 0.1 including 0.05 weight %). In another embodiment, the compound of the present invention may be used in fine perfumery in amounts from 0.001 to 30 weight percent (e.g. up to about 10 or up to 20 weight percent), more preferably between 0.01 and 5 weight percent. However, these values are given only by way of example, since the experienced perfumer may also achieve effects or may create novel accords with lower or higher concentrations.

In one embodiment there is provided a perfumed article comprising an acceptable amount of at least one compound of formula (I), or a mixture thereof. For example, the fragranced article may comprise 0.000001 weight % to 90 weight % (including 0.00001 weight %; 0.0001 weight %, 0.001 weight %, 0.01 weight %, 0.05 weight %, 0.1 weight %, 0.5 weight %, 1 weight %, 5 weight %, 8 weight %, 10 weight %, 15 weight %, 20 weight %, 25 weight %, 30 weight %, 50 weight %, 60 weight %, 65 weight %) based on the total amount of the article.

The compounds as described herein above may be employed in a consumer product base simply by directly mixing the compound of the present invention, or a perfume composition comprising the compound of the present invention, or a mixture thereof, with the consumer product base, or it may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, and then mixed with the consumer product base.

Thus, the invention additionally provides a method of manufacturing a perfumed article, comprising the incorporation of a compound of the present invention, as a fragrance ingredient, either by directly admixing the compound to the consumer product base or by admixing a perfume composition comprising the compound of the present invention, which may then be mixed with a consumer product base, using conventional techniques and methods. Through the addition of an olfactory acceptable amount of the compound of the present invention as hereinabove described the odor notes of a consumer product base will be improved, enhanced, or modified.

Thus, the invention furthermore provides a method to confer, enhance, improve or modify the hedonic properties of a perfume composition or a consumer product, which method comprises adding to said perfume composition or consumer product at least one compound of the invention.

As used herein, "consumer product base" means a composition for use as a consumer product to fulfill specific actions, such as cleaning, softening, and caring or the like. Examples of such products include fine perfumery, e.g. perfume and eau de toilette; fabric care, household products and personal care products such as cosmetics, laundry care detergents, rinse conditioner, personal cleansing composition, detergent for dishwasher, surface cleaner; laundry products, e.g. softener, bleach, detergent; body-care products, e.g. shampoo, shower gel; air care products (includes products that contain preferably volatile and usually pleasant-smelling compounds which advantageously can even in very small amounts mask unpleasant odors). Air fresheners for living areas contain, in particular, natural and synthetic essential oils such as pine needle oils, citrus oil, *eucalyptus* oil, lavender oil, and the like, in amounts for example of up to 50% by weight. As aerosols they tend to contain smaller amounts of such essential oils, by way of example less than 5% or less than 2% by weight, but additionally include compounds such as acetaldehyde (in particular, <0.5% by weight), isopropyl alcohol (in particular, <5% by weight), mineral oil (in particular, <5% by weight), and propellants.

Cosmetic products include:

(a) cosmetic skincare products, especially bath products, skin washing and cleansing products, skincare products, eye makeup, lip care products, nail care products, intimate care products, foot care products;

(b) cosmetic products with specific effects, especially sunscreens, tanning products, de-pigmenting products, deodorants, antiperspirants, hair removers, and shaving products;

(c) cosmetic dental-care products, especially dental and oral care products, tooth care products, cleaners for dental prostheses, adhesives for dental prostheses; and (d) cosmetic hair care products, especially hair shampoos, hair care products, hair setting products, hair-shaping products, and hair coloring products.

EXAMPLES

The present invention is now described in further detail by the following, non-limiting examples. All products were purified after work-up by either flash chromatography (FC) using Tsingdao Haiyang Chemical silica gel (200±300 mesh), silica gel Merck grade (60 Å) or distillation. Unless otherwise noted, mixtures of pentane and methyl tert-butyl ether (MTBE) were used as eluent. $^1$H and $^{13}$C NMR spectra were measured in CDCl$_3$. $^1$H NMR spectra in CDCl$_3$ were referenced to the residual hydrogen signal of the deuterated solvent ($^1$H 7.26 ppm, $^{13}$C 77.0 ppm) and are reported as follows: chemical shifts (δ ppm), coupling constants J in Hz. GC-MS analyses were run on a MSD5975 mass spectrometer and are reported as m/z list (relative intensity). Electron ionization (EI) was run at 70 eV. Optical rotations were measured on a polarimeter MCP 200 from Anton Paar using a sample cell (100 mm long, 3 mm diameter) and a light source from Phillips 7388 6 V 20 W. Odour description refers to the odour of the isomeric mixture of the compounds unless otherwise indicated.

Example 1: 3-(4-(2-Hydroxy-2-methylpropyl)cyclohex-1-en-1-yl)propanal a) Methyl 2-(4-oxocyclohexyl)acetate: An autoclave was charged with methyl 2-(4-hydroxyphenyl)acetate (100 g, 602 mmol, 1.0 equiv), 5% Pd/C (5.0 g, 2.35 mmol, 0.4 mol %) and ortho-xylene (400 mL). The reaction mixture was then sealed, flushed 3 times with H$_2$ and stirred at 140° C. under an atmosphere of H$_2$ (10 bar) for 48 hours. Since the reaction still contained some starting material according to GC, more 5% Pd/C (2.0 g, 0.94 mmol, 0.16 mol %) was added to the reaction mixture and the hydrogenation was continued under the same conditions (10 bar H$_2$, 140° C.) for another 24 hours. The reaction mixture was allowed to cool to room temperature and filtered to afford a crude, yellow liquid (115 g). Fractional distillation over a 10 cm Vigreux column (0.1 mbar) afforded a 1:2 mixture of methyl 2-(4-hydroxycyclohexyl)acetate and methyl 2-(4-oxocyclohexyl)acetate (96.1 g, 94%) as a colorless liquid.

To a solution of 50 grams of this mixture in CH$_2$Cl$_2$ (300 mL) was added dropwise at 0° C. a solution of pyridinium chlorochromate (PCC, 52.6 g, 0.24 mmol, 0.8 equiv) in CH$_2$Cl$_2$ (150 mL). After stirring for 2 hours at room temperature, the reaction mixture was filtered over silica gel and the solvent was removed under reduced pressure to give 46.7 g of a dark, green liquid. The crude was distilled over a 3 cm Vigreux column (0.05 mbar) to give methyl 2-(4-oxocyclohexyl)acetate (41.7 g, 83% yield) as a colorless liquid. $^1$H NMR (400 MHz, CDCl$_3$): δ 3.63 (s, 3H), 2.38-2.16 (m, 7H), 2.09-1.96 (m, 2H), 1.50-1.33 (m, 2H) ppm. $^{13}$C NMR (101 MHz, CDCl$_3$): δ 210.9, 172.6, 51.5, 40.4, 39.8, 32.9, 32.2 ppm. GC-MS (EI) m/z (%): 170 (10, [M]$^+$), 139 (21), 97 (47), 96 (100), 81 (11), 74 (22), 59 (17), 55 (54), 43 (12), 41 (21), 39 (16). bp 88° C. (0.05 mbar). Odour description: odourless, then very weak, raspberry.

b) Methyl 2-(4-allylcyclohex-3-en-1-yl)acetate: To a suspension of methyl 2-(4-oxocyclohexyl)acetate (32.1 g, 189 mmol, 1.0 equiv) and zinc powder (27.1 g, 415 mmol, 2.2 equiv) in THF (300 mL) was added dropwise at room temperature allyl bromide (35.9 mL, 415 mmol, 2.2 equiv). Since the reaction temperature rose to 65° C., the reaction mixture was cooled with an ice bath. After stirring for 16 hours at room temperature, the reaction mixture was quenched with ice cold NH$_4$Cl (120 mL) and extracted with MTBE (2×150 mL). The combined organic layers were washed with water (150 mL), brine (150 mL), dried over MgSO$_4$, filtered and concentrated under reduced pressure to give crude methyl 2-(4-allyl-4-hydroxycyclohexyl)acetate (34 g, 47% pure by GC analysis) as a yellow liquid. Upon purification by fractional distillation (0.05 mbar, 150° C. oil bath), the tertiary alcohol dehydrated spontaneously to yield methyl 2-(4-allylcyclohex-3-en-1-yl)acetate (16.8 g, 46% yield) as a colorless, slightly turbid liquid.

Alternatively, the crude tertiary alcohol can be dehydrated using pTSA as follows: To a suspension of methyl 2-(4-oxocyclohexyl)acetate (26.4 g, 155 mmol, 1.0 equiv) and zinc powder (22.3 g, 341 mmol, 2.2 equiv) in THF (250 mL) was added dropwise at room temperature allyl bromide (29.5 mL, 341 mmol, 2.2 equiv). Since the reaction temperature rose significantly, the mixture was cooled with a water bath (23° C.). After stirring for 2 hours at room temperature, the reaction mixture was quenched with ice cold 2 M HCl (100 mL) and extracted with MTBE (120 mL). The organic layer was dried over $MgSO_4$, filtered and concentrated under reduced pressure to give crude methyl 2-(4-allyl-4-hydroxycyohexyl)acetate (35.6 g, 45% pure by GC analysis) as a yellow liquid.

A solution of crude methyl 2-(4-allyl-4-hydroxycyclohexyl)acetate (35.6 g, 168 mmol, 1.0 equiv) and para toluenesulfonic acid (3.19 g, 16.8 mmol, 10 mol %) in toluene (250 mL) was refluxed for 2 hours using a Dean-Stark trap. After quenching with water (100 mL) and 2 M NaOH (80 mL), the reaction mixture was extracted with MTBE (200 mL). The organic layer was dried over $MgSO_4$, filtered and concentrated under reduced pressure to give crude methyl 2-(4-allylcyclohex-3-en-1-yl)acetate (31.4 g) as a brown liquid. The crude was purified by fractional distillation using a 10 cm Vigreux column (0.05 mbar) to afford methyl 2-(4-allylcyclohex-3-en-1-yl)acetate (9.06 g, 30% yield over 2 steps) as a colorless liquid. An analytical sample was obtained by column chromatography (pentane/MTBE 50:1). $^1$H NMR (400 MHz, $CDCl_3$): δ 5.77 (tdd, 1H, J=6.9, 10.1, 17.0 Hz, 1H), 5.41-5.34 (m, 1H), 5.06-4.96 (m, 2H), 3.66 (s, 3H), 2.66 (d, J=6.8 Hz, 2H), 2.26 (d, J=7.1 Hz, 2H), 2.26-1.63 (m, 6H), 1.38-1.23 (m, 1H) ppm. $^{13}$C NMR (101 MHz, $CDCl_3$): δ 173.4, 136.7, 136.0, 120.5, 115.6, 51.4, 42.0, 40.6, 31.5, 30.6, 28.8, 27.8 ppm. GC-MS (EI) m/z (%): 194 (8, [M]$^+$), 162 (17), 121 (15), 120 (100), 105 (29), 93 (16), 92 (28), 91 (49), 79 (68), 78 (16), 77 (21). bp 93° C. (0.05 mbar). Odour description: acidic, fruity, plastic, green, pear, pineapple.

c) 3-(4-(2-Hydroxy-2-methylpropyl)cyclohex-1-en-1-yl)propan-1-ol: To a solution of methyl 2-(4-allylcyclohex-3-en-1-yl)acetate (9.06 g, 46.6 mmol, 1.0 equiv) in THF (60 mL) was added dropwise at 0° C. MeMgCl (31.0 mL, 93.0 mmol, 2.0 equiv, 3 M in THF). After stirring for 1.5 hours at room temperature and refluxing for 3 hours, the reaction mixture was quenched with ice cold $NH_4Cl$ (60 mL) and extracted with MTBE (2×60 mL). The combined organic layers were washed with water (60 mL), brine (60 mL), dried over $MgSO_4$, filtered and concentrated under reduced pressure to give crude 1-(4-allylcyclohex-3-en-1-yl)-2-methylpropan-2-ol (8.68 g) as a yellow oil.

To a solution of 9-BBN (205 mL, 103 mmol, 2.3 equiv, 0.5 M in THF) was added dropwise at 0° C. a solution of crude 1-(4-allylcyclohex-3-en-1-yl)-2-methylpropan-2-ol (8.68 g, 44.7 mmol, 1.0 equiv) in THF (60 mL). After stirring for 1.5 hours at room temperature, 2 M NaOH (45 mL, 90 mmol, 2.0 equiv) was added at 0° C. to the reaction mixture followed by the dropwise addition of $H_2O_2$ (30.4 g, 268 mmol, 6 equiv, 30% in water). After stirring for 2 hours at room temperature, the reaction mixture was poured on 2 M HCl (130 mL) and extracted with MTBE (2×150 mL). The combined organic layers were washed with water (150 mL), brine (150 mL), dried over $MgSO_4$, filtered and concentrated under reduced pressure to give crude 3-(4-(2-hydroxy-2-methylpropyl)cyclohex-1-en-1-yl)propan-1-ol (13.9 g) as a yellow liquid. The crude was purified by column chromatography (pentane/MTBE 1:1) to give 3-(4-(2-hydroxy-2-methylpropyl)cyclohex-1-en-1-yl)propan-1-ol (4.54 g, 46% yield over 2 steps) as a yellow oil. $^1$H NMR (400 MHz, $CDCl_3$): δ 5.40-5.35 (m, 1H), 3.61 (t, J=6.6 Hz, 2H), 2.23-2.10 (m, 1H), 2.09-1.87 (m, 4H), 1.86-1.56 (m, 6H), 1.51-1.35 (m, 3H), 1.34-1.22 (m, 1H), 1.22 (s, 6H) ppm. $^{13}$C NMR (101 MHz, $CDCl_3$): δ 137.1, 120.7, 71.5, 62.8, 50.2, 33.8, 33.8, 31.0, 30.5, 30.0, 30.0, 29.9, 28.3 ppm. GC-MS (EI) m/z (%): 194 (3, [M]-$H_2O$), 138 (100), 120 (33), 105 (25), 94 (32), 93 (30), 92 (52), 91 (86), 82 (31), 79 (50), 59 (31). Odour description: odourless.

d) 3-(4-(2-Hydroxy-2-methylpropyl)cyclohex-1-en-1-yl)propanal: To a solution of 3-(4-(2-hydroxy-2-methylpropyl)cyclohex-1-en-1-yl)propan-1-ol (4.54 g, 21.4 mmol, 1.0 equiv) in $CH_2Cl_2$ (50 mL) was added at room temperature pyridinium chlorochromate (PCC, 5.53 g, 25.7 mmol, 1.2 equiv). After stirring for 45 min at room temperature, the reaction mixture was filtered over silica gel and concentrated under reduced pressure to give crude 3-(4-(2-hydroxy-2-methylpropyl)cyclohex-1-en-1-yl)propanal (3.28 g) as a brown liquid. The crude was purified by column chromatography (pentane/MTBE 1:1) to give 3-(4-(2-hydroxy-2-methylpropyl)cyclohex-1-en-1-yl)propanal (1.64 g, 37% chem. yield). Kugelrohr distillation under high vaccum (130° C. at 0.04 mbar) afforded 3-(4-(2-hydroxy-2-methylpropyl)cyclohex-1-en-1-yl)propanal (1.30 g, 30% olfact. yield) as a colorless oil. $^1$H NMR (400 MHz, $CDCl_3$): δ 9.73 (t, J=2.0 Hz, 1H), 5.38-5.33 (m, 1H), 2.54-2.46 (m, 2H), 2.29-2.22 (m, 2H), 2.21-2.10 (m, 1H), 2.08-1.95 (m, 1H), 1.95-1.85 (m, 1H), 1.85-1.77 (m, 1H), 1.76-1.61 (m, 2H), 1.46 (dd, J=5.0 Hz, 14.3 Hz, 1H), 1.39 (dd, J=5.6, 14.2 Hz, 1H), 1.34-1.23 (m, 2H), 1.22 (s, 6H) ppm. $^{13}$C NMR (101 MHz, $CDCl_3$): δ 202.7, 135.4, 121.4, 71.5, 50.1, 41.8, 33.7, 30.8, 30.1, 29.9, 29.8, 29.7, 28.5 ppm. GC-MS (EI) m/z (%): 192 (1, [M]$^+$—$H_2O$), 136 (35), 119 (21), 118 (100), 117 (37), 93 (26), 92 (72), 91 (37), 82 (22), 79 (22), 59 (39). Odour description: floral, green, fatty, aldehydic, muguet. GCTH: 0.0099 ng.

Example 2: 3-(4-(2-Hydroxy-2-methylpropyl)-2-methylcyclohex-1-en-1-yl)propanal and rel-3-((4R,6S)-4-(2-hydroxy-2-methylpropyl)-6-methylcyclohex-1-en-1-yl)propanal a) Methyl 2-(3-methyl-4-oxocyclohexyl)acetate: An autoclave was charged with methyl 2-(4-hydroxy-3-methylphenyl)acetate (15.2 g, 84.3 mmol, 1.0 equiv), 10% Pd/C (1.0 g, 0.94 mmol, 1.1 mol %) and xylenes (50 mL). The reaction mixture was then sealed, flushed 3 times with $H_2$ and stirred at 150° C. under an atmosphere of $H_2$ (100 bar) for 40 hours. Since the reaction still contained some starting material according to GC, the reaction mixture was filtered and the filtercake was thouroughly washed with MTBE. The solvent was removed under reduced pressure. The crude (16.3 g) was resubmitted to the reaction conditions using 10% Pd/C (1.5 g, 1.41 mmol, 1.7 mol %) and xylenes (50 mL). After stirring for 40 hours at 150° C. under a hydrogen atmosphere of 120 bars, full conversion was obtained and the autoclave was allowed to cool to room temperature. The reaction mixture was filtered and the solvent was removed under reduced pressure to give a crude mixture of methyl 2-(4-hydroxy-3-methylcyclohexyl)acetate and methyl 2-(3-methyl-4-oxocyclohexyl)acetate (14.6 g) as a colorless liquid.

To a solution of crude methyl 2-(4-hydroxy-3-methylcyclohexyl)acetate (14.6 g) in $CH_2Cl_2$ (250 mL) was added at room temperature pyridinium chlorochromate (PCC, 20.3 g, 94.2 mmol, 1.1 equiv). After stirring for 3 hours at room temperature, the reaction mixture was filtered over silica gel and the solvent was removed under reduced pressure. The crude (12.3 g) was purified by Kugelrohr distillation (100° C. at 0.04 mbar) to give methyl 2-(3-methyl-4-oxocyclohexyl)acetate (8.94 g, 56% yield over 2 steps, mixture of two diastereoisomers 74:26) as a colorless liquid. An analytical sample was obtained by column chromatography (pentane/MTBE 2:1). $^1$H NMR (400 MHz, $CDCl_3$, 2:3 mixture of diastereoisomers): δ 3.68 (s, 1.2H, minor $CH_3$), 3.67 (s, 1.8H, major $CH_3$), 2.57-2.23 (m, 6H), 2.14-1.08 (m, 4H), 1.10 (d, J=7.1 Hz, 1.2H, minor $CH_3$), 0.98 (d, J=6.6 Hz, 1.8H, major $CH_3$) ppm. $^{13}$C NMR (101 MHz, $CDCl_3$, 2:3 mixture of diastereoisomers): δ 213.8, 212.4, 172.9, 172.8, 51.6, 51.6, 44.0, 41.9, 41.8, 40.8, 40.2, 39.1, 38.4, 37.2, 33.8, 33.4, 31.6, 28.8, 16.0, 14.3 ppm. GC-MS (EI) m/z (%): major: 184 (15, $[M]^+$), 111 (76), 110 (100), 81 (20), 74 (27), 69 (21), 59 (30), 55 (99), 43 (34), 41 (48), 39 (24); minor: 184 (17, $[M]^+$), 111 (37), 110 (100), 109 (13), 95 (13), 74 (16), 59 (18), 55 (61), 43 (19), 41 (28). Odour description: fruity, candy, sweet, sugar, raspberry.

b) 1-(4-Allyl-3-methylcyclohex-3-en-1-yl)-2-methylpropan-2-ol: To a suspension of methyl 2-(3-methyl-4-oxocyclohexyl)acetate (8.94 g, 48.5 mmol, 1.0 equiv) and zinc powder (6.98 g, 107 mmol, 2.2 equiv) in THF (100 mL) was added dropwise at room temperature allyl bromide (9.24 mL, 107 mmol, 2.2 equiv). Since the reaction temperature rose to 36° C., the mixture was cooled with a water bath (23° C.). After stirring for 2 hours at room temperature, the reaction mixture was quenched with ice cold 2 M HCl (70 mL) and extracted with MTBE (820 mL). The organic layer was washed with water (80 mL) and brine (80 mL), dried over $MgSO_4$, filtered and concentrated under reduced pressure to give crude methyl 2-(4-allyl-4-hydroxy-3-methylcyclohexyl)acetate (11.1 g, 34% pure by GC analysis) as a yellow liquid. A solution of crude 2-(4-allyl-4-hydroxy-3-methylcyclohexyl)acetate (11.1 g, 49 mmol, 1.0 equiv) and para toluenesulfonic acid (0.93 g, 4.9 mmol, 10 mol %) in toluene (100 mL) was refluxed for 2 hours using a Dean-Stark trap. After quenching with water (60 mL) and 2 M NaOH (40 mL), the reaction mixture was extracted with MTBE (80 mL). The organic layer was dried over $MgSO_4$, filtered and concentrated under reduced pressure to give crude methyl 2-(4-allyl-3-methylcyclohex-3-en-1-yl)acetate (9.53 g) as a brown liquid.

To a solution of crude methyl 2-(4-allyl-3-methylcyclohex-3-en-1-yl)acetate (9.53 g, 45.8 mmol, 1.0 equiv) in THF (80 mL) was added dropwise at 0° C. MeMgCl (31.0 mL, 93.0 mmol, 2.0 equiv, 3 M in THF). After stirring for 1.5 hours at room temperature, the reaction mixture was quenched with ice cold $NH_4Cl$ (100 mL) and extracted with MTBE (120 mL). The combined organic layers were washed with water (100 mL), brine (100 mL), dried over $MgSO_4$, filtered and concentrated under reduced pressure to give crude 1-(4-allyl-3-methylcyclohex-3-en-1-yl)-2-methylpropan-2-ol (8.32 g) as a brown oil. The crude product was purified by column chromatography (pentane/MTBE 4:1) to furnish 1-(4-allyl-3-methylcyclohex-3-en-1-yl)-2-methylpropan-2-ol (2.4 g, 24% yield over 3 steps) as a brown oil. $^{13}$C NMR (126 MHz, $CDCl_3$): δ 136.4, 127.3, 126.9, 114.3, 71.6, 50.4, 40.5, 37.6, 31.4, 30.7, 30.2, 29.9, 29.6, 18.9 ppm. GC-MS (EI) m/z (%): 208 (1, $[M]^+$), 135 (22), 134 (100), 119 (61), 105 (41), 93 (72), 92 (21), 91 (43), 79 (20), 59 (37), 41 (28).

c) 3-(4-(2-Hydroxy-2-methylpropyl)-2-methylcyclohex-1-en-1-yl)propanal: To a solution of 9-BBN (53.0 mL, 26.5 mmol, 2.3 equiv, 0.5 M in THF) was added dropwise at 0° C. a solution of 1-(4-allyl-3-methylcyclohex-3-en-1-yl)-2-methylpropan-2-ol (2.40 g, 11.5 mmol, 1.0 equiv) in THF (30 mL). After stirring for 1.5 hours at room temperature, 2 M NaOH (11.5 mL, 23.0 mmol, 2.0 equiv) was added at 0° C. to the reaction mixture followed by the dropwise addition of $H_2O_2$ (7.84 g, 69.1 mmol, 6 equiv, 30% in water). After stirring for 2 hours at room temperature, the reaction mixture was poured on 2 M HCl (30 mL) and extracted with MTBE (50 mL). The combined organic layers were washed with water (40 mL), brine (40 mL), dried over $MgSO_4$, filtered and concentrated under reduced pressure to give crude 3-(4-(2-Hydroxy-2-methylpropyl)-2-methylcyclohex-1-en-1-yl)propan-1-ol (3.86 g) as a brown oil. The crude was purified by column chromatography (pentane/MTBE, 1:1→1:2) to give 3-(4-(2-hydroxy-2-methylpropyl)-2-methylcyclohex-1-en-1-yl)propan-1-ol (1.00 g, 38% yield) as a yellow oil.

To a solution of 3-(4-(2-hydroxy-2-methylpropyl)-2-methylcyclohex-1-en-1-yl)propan-1-ol (1.00 g, 4.42 mmol, 1.0 equiv) in $CH_2Cl_2$ (20 mL) was added at room temperature pyridinium chlorochromate (PCC, 1.14 g, 5.30 mmol, 1.2 equiv). After stirring for 1 hour at room temperature, the reaction mixture was filtered over silica gel and concentrated under reduced pressure to give crude 3-(4-(2-hydroxy-2-methylpropyl)-2-methylcyclohex-1-en-1-yl)propanal (1.55 g) as a yellow solid. The crude was purified by column chromatography (pentane/MTBE 1:1) to give 3-(4-(2-hydroxy-2-methylpropyl)-2-methylcyclohex-1-en-1-yl)propanal (0.24 g, 24% yield, 92% pure, containing 2% of rel-3-((4R,6S)-4-(2-hydroxy-2-methylpropyl)-6-methylcyclohex-1-en-1-yl)propanal) as a colorless oil. $^1$H NMR (400 MHz, $CDCl_3$): δ 9.75 (t, J=1.9 Hz, 1H), 2.49-2.41 (m, 2H), 2.36-2.24 (m, 2H), 2.11-1.96 (m, 2H), 1.94-1.62 (m, 5H), 1.58 (s, 3H), 1.49-1.35 (m, 3H), 1.22 (s, 6H). $^{13}$C NMR (101 MHz, $CDCl_3$): δ 202.9, 127.4, 127.2, 71.5, 50.2, 42.5, 40.4, 31.2, 30.5, 30.1, 29.9, 29.3, 25.6, 18.9 ppm. GC-MS (EI) m/z (%): 206 (12, $[M]^+$—$H_2O$), 150 (50), 132 (44), 117 (90), 107 (53), 106 (100), 105 (70), 93 (30), 91 (62), 79 (31), 59 (47).

Odour description: floral muguet, with a soft creamy powdery feel and a slight fresh aldehydic facet. GCTH: 0.0033 ng d) rel-3-((4R,6S)-4-(2-hydroxy-2-methylpropyl)-6-methylcyclohex-1-en-1-yl)propanal: In the 3-(4-(2-hydroxy-2-methylpropyl)-2-methylcyclohex-1-en-1-yl)propanal of step 2c, a minor isomer (2%) was identified by GC sniff as a strong, smelling muguet odorant and was then isolated by preparative GC (GC-PREP1980, TRACE1300/1310, column VF-WAXms 0.53 mm×30 m). The structure and relative stereochemistry was determined by 2D-NMR experiments: $^1$H NMR (600 MHz, $C_6D_6$): δ 9.34 (s, 1H), 5.19 (br s, 1H), 2.17-2.06 (m, 2H), 2.06-1.90 (m, 4H), 1.89-1.78 (m, 1H), 1.67-1.52 (m, 2H), 1.37 (td, J=12.3, 5.6 Hz, 1H), 1.28-1.20 (m, 2H), 1.05 (d, J=2.3 Hz, 6H), 0.97 (d, J=7.2 Hz, 3H). $^{13}$C NMR (151 MHz, $C_6D_6$): δ 200.6, 140.0, 121.3, 70.6. 50.1, 42.0, 38.8, 34.4, 32.1, 30.2, 27.3, 25.4, 19.8 ppm. GC-MS (EI) m/z (%): 206 (1, $[M]^+$—$H_2O$) 150 (35), 117 (86), 107 (32), 106 (100), 105 (48), 93 (29), 91 (56), 79 (26), 59 (53), 41 (26).

Odor description: soft, floral, muguet, white floral, soft, fresh, aldehydic, green, citrus. GCTH: 0.003 ng/L.

Example 3: 3-(4-(2-Hydroxy-2-methylpropyl)cyclohexyl)pronanal—Comparative Example a) 3-(4-(2-Hydroxy-2-methylpropyl)cyclohexyl)propan-1-ol: An autoclave was charged with 3-(4-(2-hydroxy-2- methylpropyl)phenyl)propanal (3.00 g, 14.5 mmol, 1.0 equiv, prepared according to WO2017009175), 5% Rh/Al$_2$O$_3$ (1.50 g, 0.73 mmol, 5.0 mol %) and ethanol (30 mL). The reaction mixture was then sealed, flushed 3 times with H$_2$ and stirred at 140° C. under an atmosphere of H$_2$ (150 bar) for 16 hours. The reaction mixture was allowed to cool to room temperature and filtered. The crude (2.8 g) was purified by column chromatography (pentane/EtOAc, 1:1) to give 3-(4-(2-hydroxy-2-methylpropyl)cyclohexyl)propan-1-ol (0.80 g, 26% yield, 1:1 mixture of diastereoisomers) as a colorless oil. $^1$H NMR (400 MHz, CDCl$_3$): δ 3.61-3.52 (m, 2H), 2.10 (brs, 1H), 1.84-1.74 (m, 1H), 1.74-1.59 (m, 2H), 1.58-1.42 (m, 4H), 1.42-1.30 (m, 4H), 1.30-1.10 (m, 4H), 1.18 (s, 6H), 1.01-0.80 (m, 2H) ppm. $^{13}$C NMR (101 MHz, CDCl$_3$): δ 71.7, 71.5, 63.1, 63.0, 51.0, 47.9, 37.1, 35.2, 35.1, 34.2, 33.3, 33.3, 31.1, 30.7, 30.4, 30.1, 29.9, 29.6, 28.8 ppm. GC-MS (EI) m/z (%): isomer 1: 199 (1, [M]$^+$), 95 (13), 81 (19), 80 (8), 79 (9), 67 (15), 59 (100), 55 (14), 43 (12), 41 (13), 31 (8); isomer 2: 199 (1, [M]$^+$—CH$_3$), 123 (7), 95 (12), 81 (16), 79 (7), 67 (13), 59 (100), 55 (13), 43 (10), 41 (11), 31 (8). Odour description: odourless.

b) 3-(4-(2-Hydroxy-2-methylpropyl)cyclohexyl)propanal: To a suspension of pyridinium chlorochromate (PCC, 915 mg, 4.25 mmol, 1.3 equiv) and Celite (1.0 g) in CH$_2$Cl$_2$ (40 mL) was added dropwise at room temperature a solution of 3-(4-(2-hydroxy-2-methylpropyl)cyclohexyl)propan-1-ol (0.70 g, 3.27 mmol, 1.0 equiv) in CH$_2$Cl$_2$ (10 mL). After stirring for 16 hours at room temperature, the reaction mixture was filtered over silica gel and concentrated under reduced pressure. The crude (0.35 g) was purified by column chromatography (pentane/MTBE 1:1) to give 3-(4-(2-hydroxy-2-methylpropyl)cyclohexyl)propanal (0.18 g, 26% yield, 1:1 mixture of diastereoisomers) as a colorless oil. $^1$H NMR (400 MHz, CDCl$_3$): δ 9.75 (t, J=1.8 Hz, 0.5H), 9.73 (t, J=1.8 Hz, 0.5H), 2.44-2.36 (m, 2H), 1.85-1.76 (m, 1H), 1.74-1.64 (m, 2H), 1.62-1.44 (m, 5H), 1.44-1.31 (m, 5H), 1.30-1.12 (m, 2H), 1.19 (s, 6H) ppm. $^{13}$C NMR (101 MHz, CDCl$_3$): δ 203.0, 203.0, 71.6, 71.5, 50.9, 47.8, 41.9, 41.9, 41.5, 41.4, 36.8, 35.0, 34.9, 34.1, 33.0, 30.9, 30.0, 29.7, 29.2, 29.2, 28.6, 28.6 ppm. GC-MS (EI) m/z (%): diastereoisomer 1: 197 (1, [M]$^+$—CH$_3$), 121 (7), 120 (7), 95 (9), 81 (6), 79 (7), 67 (7), 59 (100), 55 (9), 43 (10), 41 (11); diastereoisomer 2: 197 (1, [M]$^+$—CH$_3$), 121 (8), 120 (10), 95 (11), 81 (8), 79 (9), 67 (9), 59 (100), 55 (12), 43 (12), 41 (13). Odour description: very weak, floral, muguet. GCTH: 0.53 ng.

Example 4: Perfumery Example of 3-(4-(2-hydroxy-2-methylpropyl)-2-methylcyclohex-1-en-1-yl)propanal and Comparison with Cyclohexal The two compounds have been blended into a reference perfume formula intended for a fresh floral fragrance to be applied in alcohol, and to be assessed on skin or blotter.

TABLE 1

| CAS-No. | compound name | Reference parts by weight | Sample A parts by weight | Sample B parts by weight |
|---|---|---|---|---|
| 6790-58-5 | AMBROFIX (3a,6,6,9a-tetramethyldodecahydronaphtho[2,1-b]furan) | 1 | 1 | 1 |
|  | BELAMBRE (50% in IPM) | 28 | 28 | 28 |
| 118-58-1 | BENZYL SALICYLATE | 25 | 25 | 25 |
| 24851-98-7 | CEPIONATE (methyl 3-oxo-2-pentylcyclopentaneacetate) | 150 | 150 | 150 |
| 259854-70-1 | COSMONE ((5E)-3-methylcyclotetradec-5-en-1-one) | 12 | 12 | 12 |
| 32480-08-3 | DIHYDRO FARNESAL ((2E,6E)-3,7,11-trimethyldodeca-2,6-dienal) | 20 | 20 | 20 |
| 103-05-9 | DIMETHYL PHENYL ETHYL CARBINOL (2-methyl-4-phenylbutan-2-ol) | 15 | 15 | 15 |
| 3025-30-7 | ETHYL DECADIENOATE | 3 | 3 | 3 |
| 105-95-3 | ETHYLENE BRASSYLATE (1,4-dioxacycloheptadecane-5,17-dione) | 80 | 80 | 80 |
| 59056-93-8 | GEORGYWOOD (1-[(2R,3S)-2,3,8,8-tetramethyl-1,2,3,4,5,6,7,8-octahydronaphthalen-2-yl]ethanone) | 55 | 55 | 55 |
| 105-87-3 | GERANYL ACETATE SYNTHETIC ([(2E)-3,7-dimethylocta-2,6-dienyl] acetate) | 25 | 25 | 25 |
| 134-28-1 | GUAIYL ACETATE (2-(3,8-dimethyl-1,2,3,4,5,6,7,8-octahydroazulen-5-yl)propan-2-yl acetate) | 40 | 40 | 40 |
| 120-57-0 | HELIOTROPINE CRYSTALS (1,3-benzodioxole-5-carbaldehyde) | 4 | 4 | 4 |
| 928-96-1 | HEXENOL-3-CIS (10% in DPG) | 3 | 3 | 3 |
| 120-72-9 | INDOLE PURE (10% in DPG) | 9 | 9 | 9 |
| 488-10-8 | JASMONE CIS (3-methyl-2-[(Z)-pent-2-enyl]cyclopent-2-en-1-one, 10% in DPG) | 15 | 15 | 15 |
| 78-70-6 | LINALOOL SYNTHETIC (3,7-dimethylocta-1,6-dien-3-ol) | 25 | 25 | 25 |
| 1637294-12-2 | NYMPHEAL (3-(4-isobutyl-2-methylphenyl)propanal) | 8 | 8 | 8 |
| 60-12-8 | PHENYL ETHYL ALCOHOL | 75 | 75 | 75 |
| 477218-42-1 | SERENOLIDE (2-(1-(3,3-dimethylcyclohexyl)ethoxy)-2-methylpropyl cyclopropanecarboxylate) | 45 | 45 | 45 |

TABLE 1-continued

| CAS-No. | compound name | Reference parts by weight | Sample A parts by weight | Sample B parts by weight |
|---|---|---|---|---|
| 1205-17-0 | TROPIONAL (3-(1,3-benzodioxol-5-yl)-2-methylpropanal) | 25 | 25 | 25 |
| | Cyclohexal (4-(4-hydroxy-4-methylpentyl)cyclohex-3-ene-1-carbaldehyde) | | | 55 |
| | Compound of example 2c | | 8 | |
| 25265-71-8 | DIPROPYLENE GLYCOL (DPG) | 137 | 129 | 82 |
| | total | 800 | 800 | 800 |

In Sample A with 1% of the compound of example 2c, the muguet floral character is clearly enhanced and pushing the green leafy aspect of the accord; and hedonically, the ingredient brings both an airy comfortable volume and diffusion to the accord, and at the same time, adds to the density and depth of the floralcy. In comparison to Cyclohexal (in Sample B), this ingredient brings a similar benefit to the accord, complementing and interacting with the other ingredients in the formula in a very similar way. This results also as a useful benefit in the current Cyclohexal ban context. The compound of example 2c was used in a smaller amount to take into account the lower GCTH value (0.0033 ng) of this molecule in comparison to the value of Cyclohexal (0.10 ng).

Example 5: 3-(4-(2-Hydroxy-2-methylpropyl)cyclohex-1-en-1-yl)-2-methylpropanal a) Methyl 2-(4-(2-(1,3-dioxolan-2-yl)propyl)cyclohex-3-en-1-yl)acetate: To a suspension of Mg turnings (8.6 g, 352 mmol, 4.0 equiv) in THF (100 mL) was added 1,2-dibromoethane (0.82 g, 4.4 mmol, 0.05 equiv) and the mixture was stirred at rt for 10 min. Then a solution of 2-(1-bromopropan-2-yl)-1,3-dioxolane (25.7 g, 132.1 mmol, 1.5 equiv, prepared according to Y. Nishio et al., *Tetrahedron Lett.* 2017, 58, 1190) in THF (100 mL) was added dropwise at room temperature and the reaction mixture was stirred room temperature for 1 h.

To a solution of methyl 2-(4-oxocyclohexyl)acetate (15 g, 88.1 mmol, 1.0 equiv) in THF (100 mL) was added dropwise at 0° C. the above prepared Grignard reagent via cannula, while maintaining the reaction temperature below 5° C. After stirring at room temperature for 2 h, the reaction mixture was cooled to 0° C. and quenched with saturated aq $NH_4Cl$ solution. The aqueous phase was extracted with EtOAc (2×400 mL). The combined organic layers were washed with water (300 mL), brine (250 mL), dried over sodium sulfate and concentrated under reduced pressure. The crude product was purified by flash column chromatography (230-400 mesh size silica gel) using 20-30% ethyl acetate in petroleum ether to afford methyl 2-(4-(2-(1,3-dioxolan-2-yl)propyl)-4-hydroxycyclohexyl)acetate (17 g, 67%) as a pale-yellow liquid.

To a solution of methyl 2-(4-(2-(1,3-dioxolan-2-yl)propyl)-4-hydroxycyclohexyl)acetate (38 g, 132 mmol, 1 equiv) in pyridine (266 mL) was added dropwise at 0° C. $POCl_3$ (18.6 mL, 199 mmol, 1.5 equiv). After stirring at −15° C. for 3 h, the reaction mixture was cooled to 0° C. and quenched with ice cold water and extracted with ethyl acetate (2×300 mL). The combined organic layers were washed with cold 1.5 N HCl (3×300 mL), water (300 mL), brine (250 mL), dried over sodium sulfate and concentrated under reduced pressure. The crude product was purified by flash column chromatography (230-400 mesh size silica gel) using 0-10% ethyl acetate in petroleum ether to afford methyl 2-(4-(2-(1,3-dioxolan-2-yl)propyl)cyclohex-3-en-1-yl)acetate (10.5 g, 28%, calculated 19% over 2 steps) as a colourless liquid along with unreacted methyl 2-(4-(2-(1,3-dioxolan-2-yl)propyl)-4-hydroxycyclohexyl)acetate (10 g). $^1H$ NMR (400 MHz, $CDCl_3$): δ 5.37 (br s, 1H), 4.69 (t, J=4.1 Hz, 1H), 4.00-3.80 (m, 4H), 3.67 (s, 3H), 2.26 (d, J=7.1 Hz, 2H), 2.24-1.65 (m, 9H), 1.37-1.20 (m, 1H), 0.85 (dd, J=6.75, 2.25 Hz, 3H) ppm.

b) 1-(4-(2-(1,3-Dioxolan-2-yl)propyl)cyclohex-3-en-1-yl)-2-methylpropan-2-ol: To a stirred solution of methyl 2-(4-(2-(1,3-dioxolan-2-yl)propyl)cyclohex-3-en-1-yl)acetate (11.7 g, 43.6 mmol, 1 equiv) in THF (270 mL) was added 3M methyl magnesium chloride in THF (50.8 mL, 152.6 mmol, 3.5 equiv) at 0° C. After stirring for 1 h at room temperature, the reaction mixture was quenched at 0° C. with saturated aq $NH_4Cl$ solution. The aqueous phase was extracted with EtOAc (2×400 mL). The combined organic layers were washed with water (300 mL), brine (250 mL), dried over sodium sulfate and concentrated under reduced pressure. The crude product was purified by flash column chromatography (230-400 mesh size silica gel) using 10-15% ethyl acetate in petroleum ether to afford 1-(4-(2-(1,3-dioxolan-2-yl)propyl)cyclohex-3-en-1-yl)-2-methylpropan-2-ol (9.4 g, 80%) as a colourless liquid. $^1H$ NMR (400 MHz, DMSO-de): δ 5.32 (br s, 1H), 4.58 (dd, J=4.13, 3.00 Hz, 1H), 4.04 (s, 1H), 3.90-3.71 (m, 4H), 2.19-2.04 (m, 2H), 2.00-1.53 (m, 7H), 1.39-1.12 (m, 3H), 1.09 (s, 6H), 0.77 (dd, J=6.69, 1.31 Hz, 3H).

c) 3-(4-(2-Hydroxy-2-methylpropyl)cyclohex-1-en-1-yl)-2-methylpropanal: To a stirred solution of 1-(4-(2-(1,3-dioxolan-2-yl)propyl)cyclohex-3-en-1-yl)-2-methylpropan-2-ol (4.1 g, 15.2 mmol, 1 equiv) in acetonitrile (82 mL) was added at 70° C. a solution of CAN (oric ammonium nitrate, 18.4 g, 33.6 mmol, 2.2 equiv) in $H_2O$ (82 mL). Within 5 minutes the colour of the reaction mixture turned from deep red to colourless. After completion of reaction, the reaction mixture was diluted with $H_2O$ (200 mL) and aqueous phase was extracted with ethyl acetate (2×400 mL). The combined organic layers were washed with water (200 mL), brine (200 mL), dried over sodium sulfate and concentrated under reduced pressure. The crude product was purified by flash column chromatography (230-400 mesh size silica gel) using 10-15% ethyl acetate in petroleum ether to afford 3-(4-(2-hydroxy-2-methylpropyl)cyclohex-1-en-1-yl)-2-methylpropanal (1.0 g, 29%) as a colourless liquid. $^1H$ NMR (400 MHz, $CDCl_3$): δ 9.58 (d, J=1.7 Hz, 1H), 5.41-5.34 (m, 1H), 2.48 (mc, 1H), 2.39-2.28 (m, 1H), 2.23-2.08 (m, 1H), 2.04-1.58 (m, 6H), 1.41 (mc, 2H), 1.33-1.17 (m, 2H), 1.21 (d, J=1.0 Hz, 6H), 1.01 (d, J=6.9 Hz, 3H) ppm. $^{13}C$ NMR (101 MHz, CDCl$_3$, 1:1 mixture of 2 diastereoisomers): δ 205.3, 133.9, 133.9, 123.4, 123.4, 71.4, 50.0, 44.3, 44.2, 38.8, 38.7, 33.7, 33.7, 30.8, 30.7, 30.0, 30.0, 29.9, 29.7, 28.2, 28.2, 13.3, 13.2 ppm. GC-MS (EI) m/z (%): 206 (1, [M]$^+$ —H$_2$O), 150 (45), 133 (37), 132 (100), 117 (75), 93 (60), 92 (93), 91 (52), 79 (37), 59 (61), 43 (33). Odor description: floral, muguet, cyclohexal, white floral, transparent, clean. GCTH: 0.018 ng/L.

The invention claimed is:
1. A compound according to formula (I) in the form of any one or more of its stereoisomers or a mixture thereof

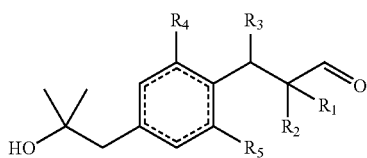

formula (I)

wherein
------ represents a carbon-carbon single or double bond, with the proviso that the compound has one carbon-carbon double bond or two isolated or conjugated carbon-carbon double bonds, and
R$_1$ to R$_5$ are independently from each other selected from H and Me,
with the proviso that the compound is not 3-(4-(2-hydroxy-2-methylpropyl) cyclohex-1-en-1-yl) propanal.

2. The compound according to claim 1, represented by formula II, in the form of any one or more of its stereoisomers or a mixture thereof

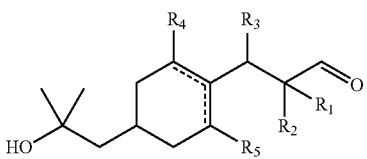

formula (II)

wherein
------ represents a carbon-carbon single or double bond, with the provision that the compound has one carbon-carbon double bond, and
R$_1$ to R$_5$ are independently from each other selected from H and Me.

3. The compound of claim 1 selected from the group consisting of: 3-(4-(2-hydroxy-2-methylpropyl)-2-methyl-cyclohex-1-en-1-yl) propanal, rel-3-((4R,6S)-4-(2-hydroxy-2-methylpropyl)-6-methylcyclohex-1-en-1-yl) propanal and 3-(4-(2-hydroxy-2-methylpropyl) cyclohex-1-en-1-yl)-2-methylpropanal.

4. A fragrance comprising a compound of formula (1) of claim 1.

5. A perfume composition comprising a compound according to formula (I) of claim 1.

6. A perfume composition according to claim 5, further comprising at least one known odourant.

7. A perfumed article comprising a compound of formula (I) of claim 1.

8. The perfumed article according to claim 7, selected from the group consisting of: fine fragrance, a personal care produce and a household care product.

9. A consumer product comprising a compound of formula (I) of claim 1.

10. The consumer product according to claim 6 selected from the group consisting of: fine perfumery, household products, laundry products, body care products, cosmetic and air care products.

11. A method to confer, enhance, improve or modify the hedonic properties of a perfume composition or of a consumer product, which method comprises: adding to said perfume composition or said consumer product at least one compound according to formula (I) of claim 1.

12. A fragrance comprising a compound of formula (II) of claim 2.

13. A perfume composition comprising a compound of formula (II) of claim 2.

14. A perfumed article comprising a compound of formula (II) of claim 2.

15. A fragrance comprising a compound according to claim 3.

16. A perfume composition comprising a compound according to claim 3.

17. A perfumed article comprising a compound according to claim 3.

* * * * *